United States Patent [19]

Crane et al.

[11] 4,287,410
[45] Sep. 1, 1981

[54] DOUBLE PURKINJE EYE TRACKER

[75] Inventors: Hewitt D. Crane, Portola Valley; Carroll M. Steele, Los Altos, both of Calif.

[73] Assignee: SRI International, Menlo Park, Calif.

[21] Appl. No.: 15,929

[22] Filed: Feb. 28, 1979

[51] Int. Cl.³ .............................. A61B 3/10; H01J 40/14
[52] U.S. Cl. ..................................... 250/201; 250/206; 351/7
[58] Field of Search ................ 250/201, 204, 206, 221; 340/573; 351/1, 6, 7, 9, 14, 16, 39

[56] References Cited

U.S. PATENT DOCUMENTS

| | | | |
|---|---|---|---|
| 3,712,716 | 1/1973 | Cornsweet et al. | 351/6 X |
| 3,724,932 | 3/1973 | Cornsweet et al. | 351/6 X |
| 3,804,496 | 4/1974 | Crane et al. | 351/6 |
| 3,925,603 | 12/1975 | Naruse et al. | 250/201 X |
| 3,967,110 | 6/1976 | Rogers et al. | 250/201 |

*Primary Examiner*—David C. Nelms
*Assistant Examiner*—Edward P. Westin
*Attorney, Agent, or Firm*—Urban H. Faubion

[57] ABSTRACT

An eye tracker measures the point in space on which the eye is fixated. An input mirror reflects an input image into the eye and directs the Purkinje images so formed in the eye back into the eye tracker mechanism. The images are gathered by a collimating objective and directed through focusing and deflecting optics so as to be incident on light flux measuring devices (photodetectors). The optics and detectors are connected in closed loop servo systems which keep the first and fourth Purkinje images centered on their respective photodetectors, keep the input beam properly positioned in the eye, and at the same time generate signals responsive to movement of the first Purkinje image to give a measure of both translational and rotational horizontal and vertical eye movement and movement of the fourth Purkinje image to give a measure of purely horizontal and vertical eye movement. Circuitry combines the signals to generate a measure of purely translational horizontal and vertical signals. The first Purkinje image is also directed to be focused nominally at a given focal distance. Light flux measuring devices are positioned equal distances before and behind the given focal distance, whereby the output signal from the devices provides a measure of focus and axial position of the eye and the difference in output signals is used in a servo system to drive the collimating objective, thereby to focus the first Purkinje image at the given focal distance.

26 Claims, 1 Drawing Figure

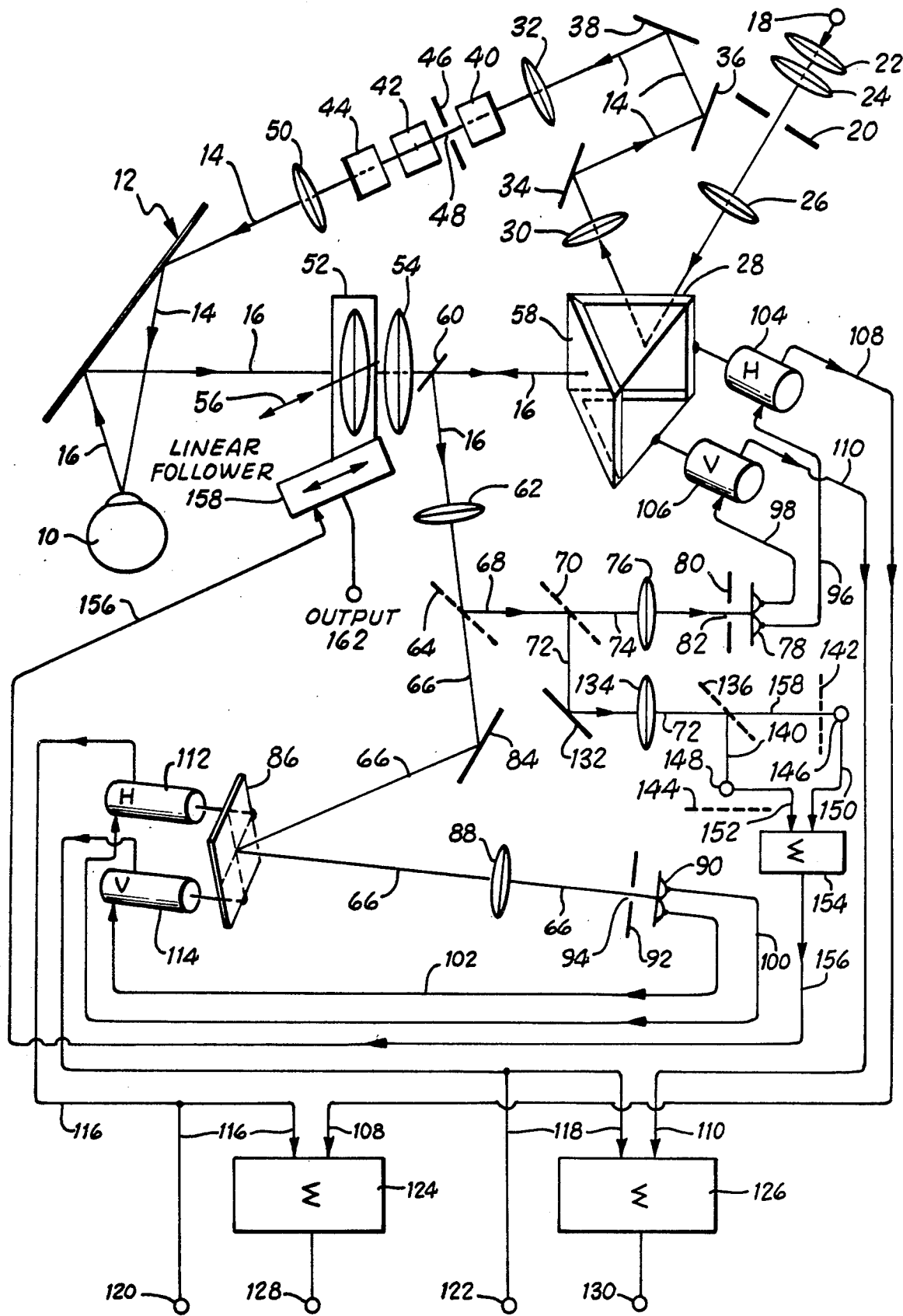

DOUBLE PURKINJE EYE TRACKER

The invention described herein was made in the course of work under a grant or award from the Department of Health, Education and Welfare.

BACKGROUND OF THE INVENTION

This invention pertains to a three dimensional eye tracker, and more particularly pertains to an eye tracker for continuously measuring the point in three dimensional space on which the eye is fixated. That is, the eye tracker continuously tracks orientation of the optic axis of the eye and movement of the eye along the axis. This is accomplished by monitoring Purkinje images formed by reflecting surfaces within the eye.

There are many areas of both research and possibilities for commercial application in which it is desirable to have available electrical signals proportional to the orientation of the optic axis of a human observer's eye. Research on the mechanics of eye movement, on many areas of visual perception and on visual search patterns would all be greatly aided by such a device. Commercial applications include the use of the eye to control other systems. For example, a computer operator might simply look at any one of a number of symbols or locations displayed in front of him and press a button, introducing the value corresponding to that location into the computer. Similarly, a servo system for controlling a gun or camera could automatically be aimed at whatever object an observer visually was fixating.

The prior art contains many methods for attempting to track eye movement. These methods, their advantages and disadvantages are dealt with at length in three United States patents assigned to Stanford Research Institute, now known as SRI International, the assignee of the present patent application, said three patents all having as one of their inventors, Hewitt D. Crane, an inventor of the present application, as follows: U.S. Pat. No. 3,712,716 issued Jan. 23, 1973 to Tom N. Cornsweet and Hewitt D. Crane for "Eye Tracker," U.S. Pat. No. 3,724,932 issued Apr. 3, 1973 to Tom N. Cornsweet and Hewitt D. Crane for "Eye Tracker and Method," and U.S. Pat. No. 3,804,496 issued Apr. 16, 1974 to Hewitt D. Crane and Tom N. Cornsweet for "Two Dimensional Eye Tracker and Method for Tracking an Eye." Reference should be had to these patents for a discussion of the early trackers. The information is not repeated here, but the subject matter of those patents is specifically incorporated herein by reference.

The information and characteristics of Purkinje images in the eye are also described in detail in the above referenced patents. Additionally, they are described in "Accurate Two-Dimensional Eye Tracker Using First and Fourth Purkinje Images" by T. N. Cornsweet and H. D. Crane, JOSA, v. 63, n. 8 (Aug. 1973), pp. 921-928, and "Accurate Three-Dimensional Eye-tracker" by H. D. Crane and C. M. Steele, App. Optics, v. 17, n. 5 (Mar. 1, 1978), pp. 691-705. In view of the full treatment of the subject of Purkinje images in these patents and articles, the information is not repeated here. The two articles, however, are also specifically incorporated herein by reference. Note also that the JOSA article describes a two dimensional Purkinje eye tracker and the Applied Optics article describes the present three dimensional Purkinje image eye tracker.

The two dimensional eye trackers disclosed and claimed in the above referenced patents have been highly successful and have solved many of the problems. For example, they do provide eye trackers which require no attachments to the eye, which produce tracking signals much more accurate than $\frac{1}{2}°$, and which are able to distinguish between translation artifacts and rotation of the eye. The eye trackers continuously monitor the orientation of the optic axis of the eye using first and fourth Purkinje images. As their designation indicates, however, the instruments only measure the direction of the visual axis and cannot accommodate axial variation in eye position.

OBJECT AND SUMMARY OF THE INVENTION

Accordingly, it is an object of this invention to provide an eye tracker for tracking eye movements through monitoring Purkinje reflections from the eye in which alignment of the subject in the tracker is relatively easy.

It is another object of this invention to provide an eye tracker for tracking eye movements through monitoring Purkinje image reflections from the eye wherein allowance is also made for axial eye movements.

It is another object of this invention to provide an eye tracker for tracking eye movements through monitoring Purkinje reflections from the eye in which the reflections from the eye are focused in the eye tracker as the eye is displaced or moved axially.

It is still another object of the invention automatically to provide such focus into the eye tracker mechanism without changing the optical magnification or shifting the location of the images in the eye.

Briefly, in accordance with one embodiment of the invention, an eye tracker is provided for tracking orientation of the optic axis of an eye and also obtaining information relative to the position of the eye along its axis. An input beam is directed along a given axis to a fixed input mirror which directs the beam into the eye of a subject so that a plurality of Purkinje images is formed by reflecting surfaces within the eye and reflected back into the eye tracker by the input mirror. A movable objective collimating lens directs the Purkinje images into the eye tracker mechanism, and two of the Purkinje images are monitored by providing deflecting means in series for imaging them on light flux measuring devices, or photodetectors. Servo systems are provided which are responsive to the photodetecting means for moving the deflecting means so that the Purkinje images are centered on their respective photodetectors. Therefore, monitoring orientation of the deflecting means gives an indication of where the eye is looking, i.e., the orientation of the optic axis of the eye. Focus of the images in the eye tracker mechanism is provided by incorporating a means to receive the beam from the deflecting means and to focus the images nominally at a specific focal distance from the input and providing means to direct light from the beam a specific distance before and after the focal distance onto the surface of the light flux density measuring devices which generate electrical signals. The difference of these signals, a measure of the condition of focus of the images, drives the movable objective collimating lens along an axis parallel to the axis of the input beam striking the fixed input mirror. In order to assure that the input light beam remains centered, a movable deflecting means is fixed to the first of the series of deflecting means at a specific angle, so that it is redirected in fixed relation thereto.

The novel features which are believed to be characteristic of the invention are set forth with particularly in the appended claims. The invention itself, however, both as to its organization and method of operation, together with further objects and advantages thereof, may best be understood by reference to the following description taken in connection with the accompanying drawing.

BRIEF DESCRIPTION OF THE DRAWING

FIG. 1 is partially a perspective and partially a diagrammatic illustration of one embodiment of a three dimensional eye tracker.

DESCRIPTION OF THE PREFERRED EMBODIMENT

As previously indicated, formation and location of Purkinje images are too well covered in the art for full description here. Since the first and fourth are important to the operation, however, a few words are in order.

As light passes through an eye, reflections occur at every interface at which there is a change in dielectric constant. There are, in particular, four surfaces where such reflections occur. The images formed by these reflections are well known and are generally referred to as Purkinje images. The virtual image of a light source that is formed by light reflected from the front of the cornea is referred to as the first Purkinje image, or simply the corneal reflection. The fourth Purkinje image is formed by light reflected from the rear surface of the eye lens where the lens forms an interface with the vitreous humor that fills the bulk of the eyeball. This rear surface of the lens acts as a concave mirror, forming a real image of the source.

The fourth Purkinje image is almost the same size and is formed in almost exactly the same plane as the first Purkinje image, though it is over 100 times less intense. If the eye undergoes translation, such as a lateral head movement, both the first and fourth Purkinje images move together through the same distance and direction that the eye moves. If, on the other hand, the eye rotates either horizontally or vertically, the two images change their separation in space because the surfaces that form the first and fourth Purkinje images have centers of curvature that lie at different distances from the center of rotation of the eye. Referred to a fixed point in space, both images move in the direction of rotation of the eye, but they move by different amounts. The physical separation between these two images in space is a measure of the angular rotation of the eye in the direction of the shift, and the measure is nominally uncontaminated by lateral movements.

The improved double Purkinje image eye tracking system is shown in the single FIGURE (FIG. 1). This version, which combines many substantial improvements over the earlier instruments, greatly expands and extends their performance and is easier to use. The eye 10 of a subject is situated at some distance in front of a fixed input and reflecting dichroic mirror 12 which transmits visible and reflects infrared light. A display (not shown) is provided behind the dichroic mirror to present a visual field to the eye 10. The display may include a number of different areas to which the eye 10 may be visually directed, with the movements of the eye being tracked and used to initiate some control function. The infrared Purkinje images are formed in the eye 10 by incident infrared light beam 14, which is brought to the input mirror 12 on a fixed axis. The Purkinje images are reflected from the input mirror 12 into the eye tracker mechanism on Purkinje image beam 16.

Consider the formation of the input infrared light beam 14. A solid state light source 18 with a narrow spectral band centered at 0.93 $\mu$m wavelength generates the beam 14. Although not illustrated, in the practical eye tracker light from the source 18 is electronically chopped at high frequency (4 kHz) to avoid the effects of room light and to use ac coupled amplifiers in the Purkinje image servo systems, thereby improving stability and decreasing noise. The light source 18 is imaged onto the plane of an iris diaphragm 20, which is conjugate with the pupil of the subject's eye 10, by a pair of lenses 22 and 24. In order to collimate the light emerging from the iris 20, a collimating lens 26 is positioned one focal length therefrom. This collimated light is reflected from a gimbaled and servoed mirror 28 and imaged by lens 30. We assume for the moment that mirror 28 is fixed, and its structure and relation to other mirrors are ignored for now.

Another lens 32 is positioned one focal length from the image of the light source formed by lens 30, and the required path length (the sum of their focal lengths) between them is obtained by the multiple reflections provided by three mirrors 34, 36 and 38. The odd number of reflections (three) from these mirrors provides an inversion of the horizontal component of the input light path of beam 14. This inversion is necessary for the proper functioning of gimbaled input path mirror 28, by means of which, as described later, the input light beam 14 is made automatically to track any change in position of the eye 10. An inversion of the vertical component of the illumination beam 14 is also necessary for proper input light tracking. Therefore, there is another mirror system which includes three mirrors 40, 42 and 44, arranged in what may be termed a Dove mirror system. This name is used because the mirrors are arranged to function like a Dove prism, which keeps the axis of the exit beam the same as that of the input beam but provides an inversion.

In order to determine the size and shape of the Purkinje images formed at the eye 10, a stop 46 having a circular aperture 48 approximately 1 inch in diameter is provided within the Dove mirror system, between the first two mirrors 40 and 42. Light which is collimated with respect to the image of the aperture 48 is delivered to the eye 10 by inserting a lens 50 between the eye 10 and the stop 46, with its focal plane at both. Thus, the eye 10 is illuminated by the light coming from the light emitting diode 18. As previously indicated, stationary dichroic mirror 12 reflects both the illumination light on input beam 14 into the eye 10 and the light from the Purkinje images (including the first and fourth) that form in the subject's eye into the eye tracker on eye tracker input beam 16.

The Purkinje images are formed nominally in the pupil plane of the eye 10 which is in the focal plane of movable eye tracker mechanism objective lens 52. Thus, light from the Purkinje images is collimated between objective lens 52 and the next adjacent focusing lens 54, which, as will be seen below, can also be considered an input focusing lens of the system, establishing a reference focal plane, or distance, for the focus control system. It also will be noted that eye tracker objective collimating lens 52 is mounted for movement off axis along arrows labeled 56 in the FIGURE but with a component along its (the len's) axis. This action is for focusing, as is explained in more detail below.

Again following the Purkinje beam 16 back into the eye tracker, the light that passes through focusing lens 54 is reflected by a gimbaled image centering mirror 58 back onto a stationary mirror 60 which is in the focal plane of focusing lens 54. Lenses 52 and 54 have the same focal length and therefore provide a unity magnification image of the pupil plane of the eye 10 at stationary mirror 60.

In order to extract and develop the information needed, it is necessary to divide, or split, the beam from the unity magnification image at stationary mirror 60 into a number of components. The best way to do this without distorting the image is to collimate the beam before splitting. Therefore, a collimating lens 62 is placed in the beam 16 reflected by mirror 60 a focal length away. The collimated light beam 16 is incident on a beam splitter 64, which passes about 90% of the beam 16 because the transmitted portion (66) of the beam 16 is used in connection with the weak fourth Purkinje image while the reflected 10% (68) is used in connection with the much stronger first Purkinje image.

Consider first the beam component 68 reflected at 90% by beam splitter 64. It is split again by beam splitter 70 which reflects (72) and transmits (74) approximately equal amounts of light. The transmitted light is imaged by focusing lens 76 onto the first Purkinje image four quadrant flux measuring device 78, which is in the focal plane of focusing lens 76. Light flux measuring device 78 is, therefore, in a plane conjugate to mirror 60, and therefore, the pupil plane of the eye 10.

The light (beam 66) which passes through beam splitter 64 to a front surface mirror 84 is reflected onto a gimbaled and servoed mirror 86.

Light reflected from gimbaled mirror 86 is collected by focusing lens 88 and focused at a second four quadrant light flux measuring device 90.

The four quadrant first Purkinje light flux measuring device 78 is provided with a stop plate 80 having an aperture 82 therein. In a similar fashion, four quadrant light flux measuring device 90 is provided with a stop plate 92 having an aperture 94 therein. The apertured plate 80 serves to mask the multiple quadrant photodetector 78 from the fourth Purkinje image but allows the first Purkinje image to pass through the aperture 82 to the light flux measuring device 78. Similarly, the apertured plate 92 serves to mask the light flux measuring device 90 from the first Purkinje image, allowing the fourth Purkinje image to impinge on the multiple quadrant photodetector 90 through the aperture 94.

The centers of the four quadrants of light flux measuring devices 78 and 92 are aligned with the apertures 82 and 94 in the first and fourth Purkinje image stop plates 80 and 92, respectively, and produce electrical output signals proportional to a shift of the incident beam from the centers of the quadrants. That is, the light flux measuring devices 78 and 90 generate electrical outputs on their electrical output circuit lines indicative of the position imbalance of the images falling thereon with respect to the four quadrants of the photodetectors. For example, an imbalance between the upper two quadrants and lower two quadrants of a photodetector is an indication that the image falling thereon is shifted with respect to the photodetector in a vertical direction. Similarly, an imbalance between the right and left pairs of quadrants of a photodetector is an indication that the image falling on the photodetector is shifted in a horizontal direction with respect to the axis of the photodetector. Thus, the first Purkinje image photodetector 78 produces a horizontal error signal at its horizontal error output circuit line 96 in response to any horizontal imbalance and a vertical error signal on circuit line 98 in response to any vertical imbalance. In like manner, fourth Purkinje image photodetector 90 produces error signals on circuit lines 100 and 102 in response to horizontal and vertical imbalances, respectively.

Gimbaled Purkinje image reflecting mirror 58 is pivoted by a pivot assembly to rotate about both vertical and horizontal axes. That is, the mirror 58 is rotatable in yaw around a vertical axis and in pitch around a horizontal axis. A horizontal servo system 104 is provided for rotating the mirror 58 in a horizontal direction (i.e., about its vertical axis) and a vertical servo system 106 is provided for rotating the mirror 58 in a vertical direction (i.e., about its horizontal axis). The horizontal servo system 104 receives as an input the position information on the electrical output circuit line 96 of the multiple quadrant photodetector 76 as to the imbalance between its horizontal pairs of quadrants, which information corresponds to horizontal displacements of the first Purkinje image with respect to the multiple quadrant photodetector 78. The horizontal servo system provides an output signal on horizontal servo signal circuit line 108 which depends upon the horizontal position of the first Purkinje image and is proportional to a combination rotation and translation of the eye 10. In a similar manner, the vertical servo system 106 receives input position information from the electrical output circuit line 98 of the multiple quadrant photodetector 78 relative to the vertical imbalance between the vertical pairs of quadrants of the photodetector, which information corresponds to vertical movement of the first Purkinje image. Vertical servo system 106 produces a signal on its output circuit 110 depending upon the vertical position of the first Purkinje image. When the first Purkinje image is at one particular point on mirror 60 (that is, in the pupil plane of the eye), it falls on the center of the four quadrant first Purkinje image light flux measuring device 78. If the image tends to move away from this point, the image at the photodetector 78 moves and the resulting error signals will drive servo motors 104 and 106 to reposition gimbaled image centering mirror 58 to bring the first Purkinje image to its initial point on stationary mirror 60, and thus on the photodetector. In this way, the image of the eye formed at stationary mirror 60 always has its corneal reflection in the same location. Also, by this arrangement Purkinje image reflecting mirror 58 maintains the first Purkinje image stationary on light flux measuring device 78, which is spatially fixed, and signals are generated indicative of both vertical and horizontal displacement of the first Purkinje image.

The fourth Purkinje image light flux measuring device, or photodetector, 90, as previously pointed out, functions simultaneously as a horizontally oriented split field cell and as a vertically oriented split field cell. Gimbaled fourth Purkinje image reflecting mirror 86 is pivoted by a pivot assembly to rotate about its central vertical and central horizontal axes. That is, the mirror 86 is pivoted at its center and is rotatable in yaw around a central vertical axis and in pitch around a central horizontal axis. A horizontal servo 112 is provided for rotating the mirror 86 in a horizontal direction (i.e., about its central vertical axis) and a vertical servo 114 is provided for rotating the mirror 86 in a vertical direction (i.e., about its central horizontal axis). Horizontal correction servo motor 112 is connected to receive the horizontal error signal (on circuit 100) generated by the photodetector 90, and vertical correction servo motor 114 is connected to receive the vertical error signal (on circuit 102). Thus, the fourth Purkinje image mirror 86 is driven so that the fourth Purkinje image is maintained in the center of the photodetector. In this manner fourth Purkinje mirror 86 is servo controlled to track movment of the fourth Purkinje image relative to the first Purkinje image.

If the eye 10 translates, the Purkinje image reflecting mirror 58 is automatically repositioned to maintain the first Purkinje image centered on the first Purkinje image photodetector 78. The same movement properly repositions the fourth Purkinje image at the center of the fourth Purkinje image photodetector 90, and therefore, no movement of the fourth Purkinje image positioning mirror 86 results. If the eye 10 rotates, however, the first and fourth Purkinje images move differentially and the proper horizontal and vertical signals are generated on the horizontal and vertical error circuit lines 100 and 102, respectively, to cause the horizontal and vertical servo motors 112 and 114 to reposition the fourth Purkinje image positioning mirror 86 so that the fourth Purkinje image is at the center of the fourth quadrant photodetector 90. Thus, the position of the fourth Purkinje image mirror 86 indicates the separation between the first and fourth Purkinje images at the pupil plane of the eye 10 and also is a measure of the two dimensional angular position of the eye 10. The horizontal and vertical servo motors 112 and 114, respectively, generate output signals which are a direct measure of the horizontal and vertical angular movement of the eye 10 and supply these outputs by way of circuit lines 116 and 118 directly to the horizontal and vertical rotational output terminals 120 and 122, respectively, and also to summing circuits 124 and 126 for processing.

The outputs at circuit lines 108 and 110, respectively, of the first Purkinje image horizontal and vertical servo motors 104 and 106 contain information relative to both eye translation and eye rotation (vertical and horizontal). This information, along with the outputs from fourth Purkinje image vertical and horizontal servo motors 114 and 112, which constitute a measure of the two dimensional angular position of the eye 10, contains all that is necessary to describe the orientation of the optic axis of the eye 10. Thus, the horizontal rotational signal on circuit line 116 (from fourth Purkinje image horizontal centering servo 112) and the signal containing both horizontal rotational and translational information (on circuit line 108) generated by first Purkinje image horizontal centering servo 104 are applied to a horizontal signal summing circuit which subtracts the rotational information to produce a pure horizontal translational output signal at its output terminal 128. In like manner, both the purely vertical rotational signal generated on output circuit 118 by fourth Purkinje image vertical servo motor 114 and the electrical signal generated by first Purkinje image vertical signal servo 106 on its output circuit line 110 are applied to vertical translational summing circuit line 126. The electrical signal on circuit line 110 contains both vertical rotational and translational information. The summing circuit 126 subtracts the vertical rotational signal on circuit line 118 to produce an output signal at its terminal 130 which contains purely vertical translational information. Thus, output terminals 120 and 122, respectively, provide pure horizontal and vertical rotational signals, and output terminals 128 and 130 of summing circuits 124 and 126, respectively, provide pure horizontal and vertical translational signals.

Note that the signals which drive the vertical servo motors 104 and 114 and horizontal servo motors 106 and 112 are generally referred to as error signals. The servo motors move until the error signals become zero. The error signals could themselves provide a direct measure of image movement without the servos, but in that form of system (generally referred to as open loop) the magnitude and the linearity of the output signals are very sensitive to factors such as component drift and change in gain in the photodetectors 78 and 90 and other circuit elements, variation in light sensitivity across the face of the photodetectors 78 and 90, and the uniformity, shape and brightness of the light pattern. The servo motors 104, 106, 112 and 114, by maintaining each image fixed at an electrically null position on their photodetectors, eliminate sensitivity to these parameters and result in a much more stable and accurate system.

Having discussed the way the signals defining eye axis orientation are derived, now consider the way a signal defining the focus of the Purkinje image delivered to the eye tracker mechanism is determined (i.e., information relative to the position of the eye in the direction of the input Purkinje image forming beam 14). Recall that the collimated beam incident on the beam splitter 70 is split, with half (beam 74) going to the first Purkinje image light flux measuring device 78 and half deflected downward (beam 72 in drawing). The light reflected downward from beam splitter 70 (beam 72) reflects from a front surface mirror 132 and is imaged by a focusing lens 134 which will focus the incident beam 72 at a given reference plane, or reference focal distance, at the focal plane of the lens. However, in order to obtain the focus information, another beam splitter 136 is used to divide the beam into two (50/50) components (138 and 140) of equal intensity which are nominally focused at focus reference planes 142 and 144 that are at the reference focal distance (the focal point of focusing lens 134).

Two focus detecting photodiodes 146 and 148 are displaced axially along beams 138 and 140, respectively, approximately 0.5 cm on either side of the reference focal distance, or reference planes of focus (142 and 144). Thus, the photodetectors 146 and 148, being small in size, measure light flux density along the axis of the imaging system, one photodetector 146 measuring light flux density behind the reference focal distance (at reference focal plane 142) and the other (photodetector 148) measuring the light flux density an equal distance in front of the reference focal distance (at reference focal plane 144). When the eye 10 is in the correct position axially, each of these photodetectors 146 and 148 receives the same amount of light, and therefore, they generate equal output signals on their respective output circuit lines 150 and 152. If the eye 10 moves axially, one or the other of these photodetectors receives more light, and the difference in light level causes the photodetectors 146 and 148 to generate different output signals on their output circuit lines 150 and 152. The photodetector on the same side of the reference focal distance with the point of focus generates the largest output signal. An error signal of proper sign and magnitude is obtained by connecting both output circuits to a comparator, or summing circuit, 154 which delivers a difference, or focal error, signal at its output circuit line 156.

In the event a focus error signal is generated on the focus error output circuit line 156, it is applied to a servo motor and linear follower 158 which repositions the focusing objective lens 52 to a point where the two focus error light flux density measuring devices 146 and 148 receive equal amounts of light. This ensures that the first Purkinje image is always in focus on the stationary mirror 60 and, consequently, first Purkinje image light flux measuring device 78, in spite of axial eye movement. Thus, the automatic focus system tracks the axial position of the eye to obtain the desired 1 cm of allowed axial variation in eye position. Without the automatic focus, intolerable blurring of the Purkinje images would occur at the first and fourth Purkinje image four quadrant light flux measuring devices 78 and 90, respectively.

It is noted that the eye tracker input objective lens 52 is driven (by its servo) along an axis 56 which is parallel to the axis of the input beam 14, not directly along its central axis. The central axis of the lens 52 is, however, maintained parallel to the eye tracker input light beam path 16 incident thereon. The reason for this arrangement is best understood by considering the focus system requirements.

The automatic focus system must meet two stringent requirements. First, any change in focus must not cause a change in optical magnification. A change in magnification would result in a change in separation of the two Purkinje images and, therefore, would be incorrectly interpreted as an eye rotation. Recall that the Purkinje images are in the focal plane of eye tracker objective lens 52 and that the light between lenses 52 and 54 is therefore collimated. Because the light is collimated, the eye 10 and objective lens 52 can both move along input light beam axis 16 without any change in magnification in the final image as long as the distance between the eye 10 and the objective lens 52 remains constant. The first step in automatic focus, therefore, is to have the axial position of objective collimating lens 50 track the axial position of the eye 10.

The second requirement of the automatic focus system is that the input light not shift if the eye 10 translates along the input light axis 14 (i.e., along the axis of the eye). If such an input light beam shift should take place while the input light beam 14 is already aimed directly at the eye 10, the shift would move the light source beam 14 away from the eye 10. In other words, the automatic focus system must be designed so eye translation along the input axis does not cause any shift in Purkinje image reflecting mirror 52, which, in turn, requires that there be no change in the position of the first Purkinje image. This is achieved by shifting eye tracker objective lens 52, not along its central axis (axis of incident beam 16), but along a path 56 parallel to the input light path 14 incident on the input reflecting mirror 12. Again, because the light between lenses 52 and 54 is collimated, an equal lateral component of shift of the eye 10 and objective lens 52 does not change the position of the final image formed by lens 54. A shift in eye position along any other axis will, however, shift the input light path appropriately as well as activate the automatic focus system.

Again recall that the signal (on circuit 156) that drives the focus servo system 158 derives from the difference in signals from focus light flux density measuring devices 146 and 148. This driving signal on circuit 156 is zero when the first Purkinje image is in focus at the reference focal distance and on first Purkinje image quadrant light flux measuring device 78. Output from the servo system that drives objective lens 52 is connected to its output terminal 162 and provides a direct measure of the axial position of the eye 10. Combined with the horizontal and vertical eye rotational position signals at output terminals 120 and 122, respectively, and vertical and horizontal eye translational position signals at output terminals 128 and 130 respectively, the three dimensional position of the globe (eye 10) can be accurately tracked.

As previously pointed out, the instrument is designed to permit up to a centimeter of eye position variation in all dimensions, horizontal, vertical and axial. For a large axial variation to be tolerated, it is necessary to incorporate automatic focus into the eye tracker (described immediately above). For large lateral variations to be tolerated, either a large input beam must be used, so the eye never moves out of the beam, or the input light path must track eye position automatically, in which case a small light source can be used. The latter option is the one chosen for this embodiment of the invention because it offers many advantages: less total light energy directed toward the eye, a crisper fourth Purkinje image because of less stray light, and improved automatic capture because the first Purkinje tracker can sometimes lock onto the iris if it is illuminated.

For automatic input path tracking, the gimbaled mirror 28 in the input light path 14 from the light source 18 is used to keep the illumination beam 14 centered on the pupil 10. For this purpose, the mirror 28 is rigidly connected to, and therefore moves in synchronism with, the Purkinje image reflecting mirror 58.

To understand how the input light is made to track eye position, note that if the eye moves upward, the corneal reflection tends to move upward on first Purkinje image photodetector 78. Error signals generated by the first Purkinje image photodetector 78, as described previously, reposition Purkinje image reflecting mirror 58 to maintain the corneal image centered on stationary Purkinje image reflecting mirror 60. Motion imparted to Purkinje image reflecting mirror 58, however, also repositions the gimbaled input light reflecting mirror 28; this automatically deflects the input illumination beam 14 upward to track the corneal reflection. However, the illumination tracking cannot be perfect with respect to the pupil of the eye because first Purkinje image photodetector 78 tracks the corneal reflection, which moves with respect to the eye pupil when the eye 10 makes rotational movements. Nevertheless, the design is such that the tracking error is less than 1 mm with eye translation of ±0.5 cm in any direction and with eye rotations of 15° in all directions (30° diameter field); that is, the input illumination beam tracks the center of the pupil to within 1 mm over this range.

A critical requirement of the input light tracking system is that a shift in the input light path 14 must not cause ay change in the angle of the input axis (incident on the eye 10) with respect to the eye axis. Any such change alters the separation of the Purkinje images and, therefore, is incorrectly interpreted as an eye rotation. There are a number of ways to avoid this situation. For example, it is possible to achieve the desired input tracking by translating the iris diaphragm 20 in the source beam. Such a translation, however, requires yet another two dimensional servo system.

In the embodiment illustrated, the correct translation of the input beam 14 incident on the eye 10 is achieved by positioning input beam deflecting mirror 28 in the collimated light path between collimating lens 26 and imaging lens 30 and attaching it rigidly to Purkinje image reflecting mirror 58, as described above. The required movement sensitivity in the input light path 14 is obtained by the proper choice of angle between input beam deflecting mirror 28 and Purkinje image reflecting mirror 58.

It will be recognized from the above description that the objects of this invention have been carried out by providing an instrument which measures, as a function of time, the point on which an eye is fixated. Nothing is attached to the subject (patient), who is easily aligned in the device. The measuring wavelength is in the near infrared and is invisible. The usable field of the instrument is greater than 20°; the horizontal and vertical directions of gaze are measured with a noise level and repeatability of about 1 min of arc. Two instruments may be aligned side by side for tracking both eyes simultaneously.

While a particular embodiment of the invention is shown, it will, of course, be understood that the invention is not limited thereto, since many modifications, both in the circuit arrangement and in the instrumentalities employed, may be made. It is contemplated that the appended claims will cover any such modifications as fall within the true spirit and scope of the invention.

What is claimed is:

1. In an improved eye tracker for continuously tracking orientation of an optic axis of an eye having a cornea and a lens, where the eye is adapted to move axially, to translate in a horizontal and a vertical direction and to rotate in a horizontal and a vertical direction, comprising light source means for forming a light beam, optical means for directing said light beam into the eye whereby light reflected by the cornea forms a first Purkinje image and light reflected by the rear of the eye lens forms a fourth Purkinje image, optical means to focus the image of at least one of the said first and fourth Purkinje images nominally at a given reference focal distance, first and second light flux density measuring devices that produce an output electrical signal which is a function of light incident thereon, and means to obtain light flux density on the said first and second light flux density measuring devices from equal distances but opposite sides of the said reference focal distance.

2. In an improved eye tracker for continuously tracking orientation of an optic axis of an eye as defined in claim 1, wherein the said means to obtain light flux density on the said first and second light flux density measuring devices comprises a light beam dividing means on the optical axis and in front of the said given reference focal distance, thereby to divide the light beam into first and second focusing light paths, the said first light flux density measuring device being positioned in the said first light path a given specific distance beyond the said given reference focal distance and the said second light flux density measuring device being positioned in the said second light path the same given specific distance in front of the said given reference focal distance as the given specific distance the said first light flux density measuring device is beyond the said given reference focal distance.

3. In an improved eye tracker for continuously tracking orientation of an optic axis of an eye as defined in claim 1, wherein the said optical means includes an objective mounted for movement in a direction having a component along its optical axis, objective position adjusting means is provided for moving the said objective back and forth, comparator means is provided for comparing the output signals generated by the said first and second light flux density measuring devices and generating a focus error output signal when the said image is focused on either side of the said given reference focal distance, and circuit means is provided for connecting the output of the said comparator means to the said objective position adjusting means, thereby to reposition the said objective and focus the said image at the said given reference focal distance.

4. In an improved eye tracker for continuously tracking orientation of an optic axis of an eye as defined in claim 2, wherein the said optical means includes an objective mounted for movement in a direction having a component along its optical axis, objective position adjusting means is provided for moving the said objective back and forth, comparator means is provided for comparing the output signals generated by the said first and second light flux density measuring devices and generating a focus error output signal when the said image is focused on either side of the said given reference focal distance, and circuit means is provided for connecting the output of the said comparator means to the said objective position adjusting means, thereby to reposition the said objective and focus the said image at the said given reference focal distance.

5. In an improved eye tracker for continuously tracking orientation of an optic axis of an eye as defined in claim 3, wherein the said objective is positioned nominally a focal distance from the said image to be focused, whereby light from the said image is collimated thereby, and a reference image focusing means is positioned to receive collimated light from the said objective and form an image at the said reference focal distance.

6. In an improved eye tracker for continuously tracking orientation of an optic axis of an eye as defined in claim 4, wherein the said objective is positioned nominally a focal distance from the said image to be focused, whereby light from the said image is collimated thereby, and a reference image focusing means is positioned to receive collimated light from the said objective and form an image at the said reference focal distance.

7. In an improved eye tracker for continuously tracking orientation of an optic axis of an eye having a cornea and a lens, where the eye is adapted to move axially, to translate in a horizontal and a vertical direction and to rotate in a horizontal and a vertical direction, comprising light source means for forming a light beam, optical means for directing said light beam into the eye whereby light reflected by the cornea forms a first Purkinje image and light reflected by the rear of the eye lens forms a fourth Purkinje image, optical means to focus the image of the said first and fouth Purkinje images nominally at the desired image plane, reference optical means to reimage at least one of the said first and fourth Purkinje images nominally at a given reference focal distance, first and second light flux density measuring devices that produce an output electrical signal which is a function of light incident thereon, and means to obtain light flux density on the said first and second light flux density measuring devices from equal distances but opposite sides of the said reference focal distance.

8. In an improved eye tracker for continuously tracking orientation of an optic axis of an eye as defined in claim 7, wherein the said means to obtain light flux density on the said first and second light flux density measuring devices comprises a light beam dividing means on the optical axis and in front of the said given reference focal distance, thereby to divide the light beam into first and second focusing light paths, the said first light flux density measuring device being positioned in the said first light path a given specific distance beyond the said given reference focal distance and the said second light flux density measuring device being positioned in the said second light path the same given specific distance in front of the said given reference focal distance as the given specific distance the said first light flux density measuring device is beyond the said given reference focal distance.

9. In an improved eye tracker for continuously tracking orientation of an optic axis of an eye as defined in claim 7, wherein the said imaging optical means includes an objective mounted for movement in a direction having a component along its optical axis, objective position adjusting means is provided for moving the said objective back and fourth, comparator means is provided for comparing the output signals generated by the said first and second light flux density measuring devices and generating a focus error output signal when the said image is focused on either side of the said given reference focal distance, and circuit means is provided for connecting the output of the said comparator means to the said objective position adjusting means, thereby to reposition the said objective and focus the said image at the said desired image plane and, consequently, the image at the said given reference focal distance.

10. In an improved eye tracker for continuously tracking orientation of an optic axis of an eye as defined in claim 8, wherein, the said imaging optical means includes an objective mounted for movement in a direction having a component along its optical axis, objective position adjusting means is provided for moving the said objective back and forth, comparator means is provided for comparing the output signals generated by the said first and second light flux density measuring devices and generating a focus error output signal when the said image is focused on either side of the said given reference focal distance, and circuit means is provided for connecting the output of the said comparator means to the said objective position adjusting means, thereby to reposition the said objective and focus the said image at the said desired image plane and, consequently, the image at the said given reference focal distance.

11. In an improved eye tracker for continuously tracking orientation of an optic axis of an eye as defined in claim 9, wherein the said objective is positioned nominally a focal distance from the said image to be focused, whereby light from the said image is collimated thereby, and a reference image focusing means is positioned to receive collimated light from the said objective and form an image at the said reference focal distance.

12. In an improved eye tracker for continuously tracking orientation of an optic axis of an eye as defined in claim 10, wherein the said objective is positioned nominally a focal distance from the said image to be focused, whereby light from the said image is collimated thereby, and a reference image focusing means is positioned to receive collimated light from the said objective and form an image at the said reference focal distance.

13. In an improved eye tracker for continuously tracking orientation of an optic axis of an eye having a cornea and a lens, where the eye can move axially, translate in a horizontal and a vertical direction and also rotate in a horizontal and a vertical direction, comprising an input reflecting mirror positioned in front of the eye at an angle to its optic axis, light source means directing a beam of light along an axis and onto the said input reflecting mirror, thereby flooding the eye with light, whereby light reflected by the cornea forms a first Purkinje image and light reflected by the rear of the eye lens forms a fourth Purkinje image, optical means positioned to receive the said first and fourth Purkinje images from the said reflecting mirror and to focus at least one of the said first and fourth Purkinje images nominally at a given reference focal distance, first and second light flux density measuring devices that produce an output electrical signal which is a function of light incident thereon, means to obtain light flux density on the said first and second light flux density measuring devices from equal distances but opposite sides of the said reference focal distance, the said optical means including an objective mounted for movement in a direction parallel to the axis of the source beam striking the said input reflecting mirror and having a component of motion along its optical axis, objective position adjusting means for moving the said objective back and forth, comparator means for comparing the output signals generated by the said first and second light flux density measuring devices and generating a focus error output signal when the said image is focused on either side of the said given reference focal distance, and circuit means for connecting the output of the said comparator means to the said objective position adjusting means, thereby to reposition the said objective along its axis of movement and focus the said image at the said given reference focal distance.

14. In an improved eye tracker as defined in claim 13, wherein the said objective is positioned nominally a focal distance from the said image to be focused, whereby light from the said image is collimated thereby, and a reference image focusing means is positioned to receive collimated light from the said objective and form an image at the said reference focal distance.

15. In an improved eye tracker for continuously tracking orientation of an optic axis of an eye having a cornea and a lens, where the eye can move axially, translate in a horizontal and a vertical direction and also rotate in a horizontal and a vertical direction, comprising an input reflecting mirror positioned in front of the eye at an angle to its optic axis, light source means directing a beam of light along an axis and onto the said input reflecting mirror, thereby flooding the eye with light, whereby light reflected by the cornea forms a first Purkinje image and light reflected by the rear of the eye lens forms a fourth Purkinje image, optical means positioned to receive the said first and fourth Purkinje images from the said reflecting mirror and to focus at least one of the said first and fourth Purkinje images nominally at a given reference focal distance, first and second light flux density measuring devices that produce an output electrical signal which is a function of light incident thereon, means to obtain light flux density on the said first and second light flux density measuring devices comprising a light beam dividing means on the optical axis and in front of the said given reference focal distance, thereby to divide the light beam into first and second focusing light paths, the said first light flux density measuring device being positioned in the said first light path a given specific distance beyond the said given reference focal distance and the said second light flux density measuring device being positioned in the said second light path the same given specific distance in front of the said given reference focal distance as the given specific distance the said first light flux density measuring device is beyond the said given reference focal distance, the said optical means including an objective mounted for movement in a direction parallel to the axis of the said source beam striking the said input reflecting mirror and having a component of movement along its optical axis, objective position adjusting means for moving the said objective back and forth, comparator means for comparing the output signals generated by the said first and second light flux density measuring devices and generating a focus error output signal when the said image is focused on either side of the said given reference focal distance, and circuit means for connecting the output of the said comparator means to the said objective position adjusting means, thereby to reposition the said objective along its axis of movement and focus the said image at the said given reference focal distance.

16. In an improved eye tracker as defined in claim 15, wherein the said objective is positioned nominally a focal distance from the said image to be focused, whereby light from the said image is collimated thereby, and a reference image focusing means is positioned to receive collimated light from the said objective and from an image at the said reference focal distance.

17. In an improved eye tracker for continuously tracking orientation of an optic axis of an eye having a cornea and a lens, where the eye can move axially, translate in a horizontal and a vertical direction and also rotate in a horizontal and a vertical direction, comprising an input reflecting mirror positioned in front of an eye at an angle to its optic axis, light source means directing a beam of light along an axis and onto the said input reflecting mirror, thereby flooding the eye with light, whereby light reflected by the cornea forms a first Purkinje image and light reflected by the rear of the eye lens forms a fourth Purkinje image, optical means positioned to receive the said first and fourth Purkinje images from the said reflecting mirror and to focus the said first and fourth Purkinje images at the desired image plane, reference optical means to reimage at least one of the said first and fourth Purkinje images nominally at a given reference focal distance, first and second light flux density measuring devices that produce an output electrical signal which is a function of light incident thereon, means to obtain light flux density on the said first and second light flux density measuring devices from equal distances but opposite sides of the said reference focal distance, the said optical means including an objective mounted for movement in a direction parallel to the axis of the source beam striking the said input reflecting mirror and having a component of motion along it optical axis, objective position adjusting means for moving the said objective back and forth, comparator means for comparing the output signals generated by the said first and second light flux density measuring devices and generating a focus error output signal when the said image is focused on either side of the said given reference focal distance, and circuit means for connecting the output of the said comparator means to the said objective position adjusting means, thereby to reposition the said objective along its axis of movement and focus the said image at the said given reference focal distance.

18. In an improved eye tracker as defined in claim 17, wherein the said objective is positioned nominally a focal distance from the said image to be focused, whereby light from the said image is collimated thereby, and a reference image focusing means is positioned to receive collimated light from the said objective and form an image at the said reference focal distance.

19. In an improved eye tracker for continuously tracking orientation of an optic axis of an eye having a cornea and a lens, where the eye can move axially, translate in a horizontal and a vertical direction and also rotate in a horizontal and a vertical direction, comprising an input reflecting mirror positioned in front of an eye at an angle to its optic axis, light source means directing a beam of light along an axis and onto the said input reflecting mirror, thereby flooding the eye with light, whereby light reflected by the cornea forms a first Purkinje image and light reflected by the rear of the eye lens forms a fourth Purkinje image, optical means positioned to receive the said first and fourth Purkinje images from the said reflecting mirror and to focus the said first and fourth Purkinje images at the desired image plane, reference optical means to reimage at least one of the said first and fourth Purkinje images nominally at a given reference focal distance, first and second light flux density measuring devices that produce an output electrical signal which is a function of light incident thereon, means to obtain light flux density on the said first and second light flux density measuring devices comprising a light beam dividing means on the optical axis and in front of the said given reference focal distance, thereby to divide the light beam into first and second focusing light paths, the said first light flux density measuring device being positioned in the said first light path a given specific distance beyond the said given reference focal distance and the said second light flux density measuring device being positioned in the said second light path the same given specific distance in front of the said given reference focal distance as the given specific distance the said first light flux density measuring device is beyond the said given reference focal distance, the said optical means including an objective mounted for movement in a direction parallel to the axis of the said source beam striking the said input reflecting mirror and having a component of movement along its optical axis, objective position adjusting means for moving the said objective back and forth, comparator means for comparing the output signals generated by the said first and second light flux density measuring devices and generating a focus error output signal when the said image is focused on either side of the said given reference focal distance, and circuit means for connecting the output of the said comparator means to the said objective position adjusting means, thereby to reposition the said objective along its axis of movement and focus the said image at the said given reference focal distance.

20. In an improved eye tracker as defined in claim 19, wherein the said objective is positioned nominally a focal distance from the said image to be focused, whereby light from the said image is collimated thereby, and a reference image focusing means is positioned to receive collimated light from the said objective and form an image at the said reference focal distance.

21. In an improved eye tracker for continuously tracking orientation of an optic axis of an eye having a cornea and a lens, where the eye is adapted to move axially, to translate in a horizontal and a vertical direction and to rotate in a horizontal and a vertical direction, comprising light source means for forming a light beam, optical means for directing said light beam into the eye, whereby light reflected by the cornea forms a first Purkinje image and light reflected by the rear of the eye lens forms a fourth Purkinje image, light flux measuring means for generating electrical signals in response to said first and fourth Purkinje light images falling thereon, first measuring means incorporating said light flux measuring means continuously to measure the spatial separation between the said first and fourth Purkinje image and thereby to develop electrical signals proportional to horizontal and vertical rotational movements of the eye, second measuring means incorporating said light flux measuring means continuously to measure movement of one of the first and fourth Purkinje images, thereby to generate electrical signals proportional both to horizontal and vertical translational and rotational movements of the eye, means to combine the said electrical signals proportional to horizontal and vertical rotational movements with the said electrical signals proportional to both vertical and horizontal translational and rotational eye movements to generate electrical signals proportional to vertical and horizontal translational eye movements, and a focusing system incorporating said light flux measuring means to measure focus at a given reference focal distance from the eye and generate an electrical signal indicative of the condition of focus.

22. In an improved eye tracker for continuously tracking orientation of an optic axis of an eye having a cornea and a lens, where the eye is adapted to move axially, to translate in a horizontal and a vertical direction and to rotate in a horizontal and a vertical direction, comprising light source means for forming a light beam, optical means for directing said light beam into the eye, whereby light reflected by the cornea forms a first Purkinje image and light reflected by the rear of the eye lens forms a fourth Purkinje image, first, second, third and fourth light flux measuring means for generating electrical signals in response to said first and fourth Purkinje light images falling thereon, centering means responsive to said electrical signals for centering the first and fourth Purkinje images respectively on the said third and fourth light flux measuring means, said centering means developing position signals indicative of the orientation of the optic axis of the eye, optical means to focus the image of at least one of the said first and fourth Purkinje images nominally at a given reference focal distance, and means to obtain light flux density on the said first and second light flux measuring devices from equal distances but opposite sides of the said reference focal distance, thereby to determine focus condition of the said image.

23. In an improved eye tracker for continuously tracking orientation of an optic axis of an eye as defined in claim 22, wherein an input reflecting mirror is positioned in front of the eye at an angle to its optic axis, said light source means directs the said beam of light along an axis, onto the said input reflecting mirror and into the eye, said optical means is positioned to receive the said first and fourth Purkinje images from the said reflecting mirror and includes an objective mounted for movement in a direction parallel to the axis of the source beam striking the said input reflecting mirror and having a component of motion along its optical axis, objective position adjusting means is provided for moving the said objective back and forth, comparator means is provided for comparing the output signals generated by the said first and second light flux measuring devices and generating a focus error output signal when the said image is focused on either side of the said given reference focal distance, and circuit means is provided for connecting the output of the said comparator means to the said objective position adjusting means, thereby to reposition the said objective along its axis of movement and focus the said image at the said given reference focal distance.

24. In an improved eye tracker as defined in claim 23, wherein the said optical means focuses both the said first and fourth Purkinje images at a desired reference plane and includes reference optical means to reimage at least one of the said first and fourth Purkinje images nominally at the said reference focal distance.

25. In an improved eye tracker as defined in claim 23, wherein the said centering means includes a gimbaled Purkinje image reflecting mirror capable of being driven in pitch and yaw about its vertical and horizontal axes, positioned in the light image path between the said input reflecting mirror and the said light flux measuring means, said gimbaled Purkinje image reflecting mirror means being driven by the electrical output signals from the third light flux density measuring means to center at least the said first Purkinje image at the said third light flux measuring means.

26. In an improved eye tracker as defined in claim 25, wherein a gimbaled source mirror capable of being driven in pitch and yaw is positioned in the path of the said input light source beam and fixed at a definite angle relative to the said Purkinje image reflecting mirror, whereby both mirrors are driven simultaneously in a fixed relationship so that the axis of the said input light source beam is affected in a definite way in response to Purkinje image centering movement of the said Purkinje image reflecting mirror.

* * * * *